United States Patent [19]

Endo

[11] Patent Number: 5,051,901

[45] Date of Patent: Sep. 24, 1991

[54] METHOD FOR JUDGING ERRORS IN APPLYING LIQUID SAMPLES DURING BIOCHEMICAL ANALYSIS

[75] Inventor: Hirotoshi Endo, Kanagawa, Japan

[73] Assignee: Fuji Photo Film Co., Ltd., Kanagawa, Japan

[21] Appl. No.: 570,078

[22] Filed: Aug. 20, 1990

[30] Foreign Application Priority Data

Aug. 21, 1989 [JP] Japan .................. 1-214463

[51] Int. Cl.$^5$ .......................................... G06F 15/00
[52] U.S. Cl. ........................... 364/413.11; 356/39; 364/497; 364/552
[58] Field of Search ............ 364/497, 413.11, 413.08, 364/413.1, 552; 356/39

[56] References Cited

U.S. PATENT DOCUMENTS

| | | | |
|---|---|---|---|
| 3,775,595 | 11/1973 | Rosse et al. | 364/413.11 |
| 4,061,469 | 12/1977 | Du Bose | 356/39 |
| 4,082,457 | 4/1978 | Kohno et al. | 356/39 |
| 4,313,735 | 2/1982 | Yamashita et al. | 364/498 |
| 4,797,000 | 1/1989 | Curtis | 356/436 |
| 4,849,340 | 7/1989 | Oberhardt | 73/864.72 |
| 4,959,796 | 9/1990 | Hidaka et al. | 356/39 |

Primary Examiner—Jerry Smith
Assistant Examiner—Laura Brutman
Attorney, Agent, or Firm—Sughrue, Mion, Zinn Macpeak & Seas

[57] ABSTRACT

Errors in applying liquid sample are judged during biochemical analysis wherein a droplet of liquid sample is applied to an analysis medium containing a reagent, which chemically reacts with a specific constitutent in the liquid sample, the analysis medium is then incubated, the optical densities of the analysis medium are determined, and concentration of the specific constituent in the liquid sample is determined from the optical densities of the analysis medium thus determined. The method for judging errors in applying a liquid sample comprises the steps of determining the optical density of the analysis medium plural times with the passage of time while the analysis medium is being incubated, and calculating the difference between the maximum value and the minimum value of the optical densities thus determined for the analysis medium. The difference is compared with a predetermined threshold value. In cases the difference is smaller than the threshold value, it is judged that errors occurred in applying a liquid sample to the analysis medium.

4 Claims, 8 Drawing Sheets

METHOD FOR JUDGING ERRORS IN APPLYING LIQUID SAMPLES DURING BIOCHEMICAL ANALYSIS

BACKGROUND OF THE INVENTION

1. Field of the Invention

This invention relates to a method for judging errors in applying a liquid sample during a biochemical analysis, with which a specific constituent in the liquid sample is analyzed chemically. This invention particularly relates to a method for judging errors in applying a liquid sample during a biochemical analysis wherein a droplet of liquid sample is applied to an analysis medium, such as a chemical analysis slide or test film, containing a reagent which reacts with the liquid sample, and the optical density, which depends on how much of a reaction product was formed by the reaction between the liquid sample and the reagent in the analysis medium, is determined.

2. Description of the Prior Art

Qualitative or quantitative analyses of specific chemical constituents in liquid samples are conducted for various industrial purposes. Particularly, it is very important in biochemical and clinical fields to be able to quantitatively analyze certain chemical or physical constituents in body fluids such as blood or urine.

Recently, as disclosed in, for example, U.S. Pat. Nos. 3,992,158 and 4,292,272, dry type chemical analysis slides were developed for use in systems designed for performing quantitative analyses, with which systems the concentration of specific chemical constituents or specific physical constituents contained in a droplet of liquid sample, which is applied to the chemical analysis slide, is determined. It is possible to analyze a liquid sample more simply and more quickly with methods in which chemical analysis slides are used than with methods in which conventional wet type analyses are carried out. Therefore, it is more desirable to use chemical analysis slides, particularly in medical organizations, research laboratories, or the like, where many samples must be analyzed, than to carry out conventional wet type analyses.

In order for a chemical analysis slide to be used in the determination of the concentration of a specific constituent contained in a liquid sample, a measured amount of the liquid sample is put on the chemical analysis slide and is kept at a predetermined temperature (i.e. incubated) for a predetermined time in an incubator, which causes a color reaction. The chemical analysis slide is then exposed to light having a wavelength which is selected in advance. The selection of the wavelength depends on the constituents of the liquid sample and the constituents of a reagent contained in the reagent layer in the chemical analysis slide. Light is thus irradiated to a reaction product which forms on the chemical analysis slide, and the amount of light reflected by the reaction product is measured. The optical density of the chemical analysis slide is then found from the measured amount of reflected light.

Also, as a means with which liquid samples can be automatically and sequentially analyzed, a novel apparatus is proposed in, for example, U.S. Pat. No. 3,526,480. In the proposed apparatus, a long tape-like test film containing a reagent is used instead of the aforesaid chemical analysis slides, and the application, incubation and measurement of samples are carried out sequentially on adjacent portions of the test film.

In general, in the biochemical analysis apparatuses utilizing the analysis medium, such as a chemical analysis slide or test film, a sample application pipette is used to apply a droplet of liquid sample to the analysis medium. The sample application pipette is immersed in a liquid sample contained in a vessel, and takes up a small amount of the liquid sample by air suction. Thereafter, the sample application pipette moves to a position above an analysis medium and applies a predetermined amount of the liquid sample to the analysis medium.

In cases errors occur in the operation of the sample application pipette, or in cases the amount of the liquid sample contained in the vessel becomes insufficient, the problem occurs in that no liquid sample is applied to an analysis medium, or only an insufficient amount of the liquid sample is applied to an analysis medium.

In the conventional biochemical analysis apparatuses utilizing the analysis medium, such as a chemical analysis slide or test film, no judgment has heretofore been made as to whether or not errors occurred in applying a liquid sample to an analysis medium. Therefore, even when a value obtained from a quantitative analysis of a specific constituent was extraordinarily small, it could not heretofore been judged whether the value obtained is correct or is small because of errors in applying the liquid sample.

SUMMARY OF THE INVENTION

The primary object of the present invention is to provide a method for judging errors in applying a liquid sample during a biochemical analysis, with which accurate judgments can be made as to whether errors occurred or did not occur in applying a liquid sample to analysis medium.

Another object of the present invention is to provide a method for judging errors in applying a liquid sample during a biochemical analysis, which makes the biochemical analysis operations reliable.

The present invention provides a method for judging errors in applying a liquid sample during a biochemical analysis wherein a droplet of liquid sample is applied to an analysis medium containing a reagent, which chemically reacts with a specific constituent in the liquid sample, the analysis medium is then incubated, the optical densities of the analysis medium are determined, and concentration of the specific constituent in the liquid sample is determined from the optical densities of the analysis media thus determined, the method for judging errors in applying a liquid sample during a biochemical analysis comprising the steps of:

i) determining the optical density of said analysis medium plural times with the passage of time while said analysis medium is being incubated, ii) calculating the difference between the maximum value and the minimum value of the optical densities thus determined for said analysis medium, iii) comparing said difference with a predetermined threshold value, and iv) in cases said difference is smaller than said threshold value, judging that errors occurred in applying a liquid sample to said analysis medium.

In general, the optical density of an analysis medium, which depends on how much of a reaction product was formed by the reaction between a liquid sample and a reagent in the analysis medium, increases gradually with the passage of time after the liquid sample is applied to the analysis medium. The extent of the increase is higher as the total amount of the specific constituent, which is to be analyzed and which is contained in the analysis medium, is larger. Therefore, in cases where the difference between the maximum value and the minimum value of the optical densities determined for an analysis medium is smaller than a threshold value, which is appropriately set in advance, it can be judged that the amount of a liquid sample, which was applied to the analysis medium, was insufficient, or that no liquid sample was applied thereto.

As described above, with the method for judging errors in applying a liquid sample during a biochemical analysis in accordance with the present invention, the optical density of an analysis medium is determined plural times with the passage of time while the analysis medium is being incubated. Thereafter, the difference between the maximum value and the minimum value of the optical densities thus determined for the analysis medium is calculated and compared with a predetermined threshold value. From the results of the comparison, an accurate judgment can be made as to whether errors occurred or did not occur in applying the liquid sample to the analysis medium. Therefore, with the method for judging errors in applying a liquid sample in accordance with the present invention, the reliability of the biochemical analysis operations can be kept high.

DESCRIPTION OF THE PREFERRED EMBODIMENTS

The present invention will hereinbelow be described in further detail with reference to the accompanying drawings.

Figure 2:
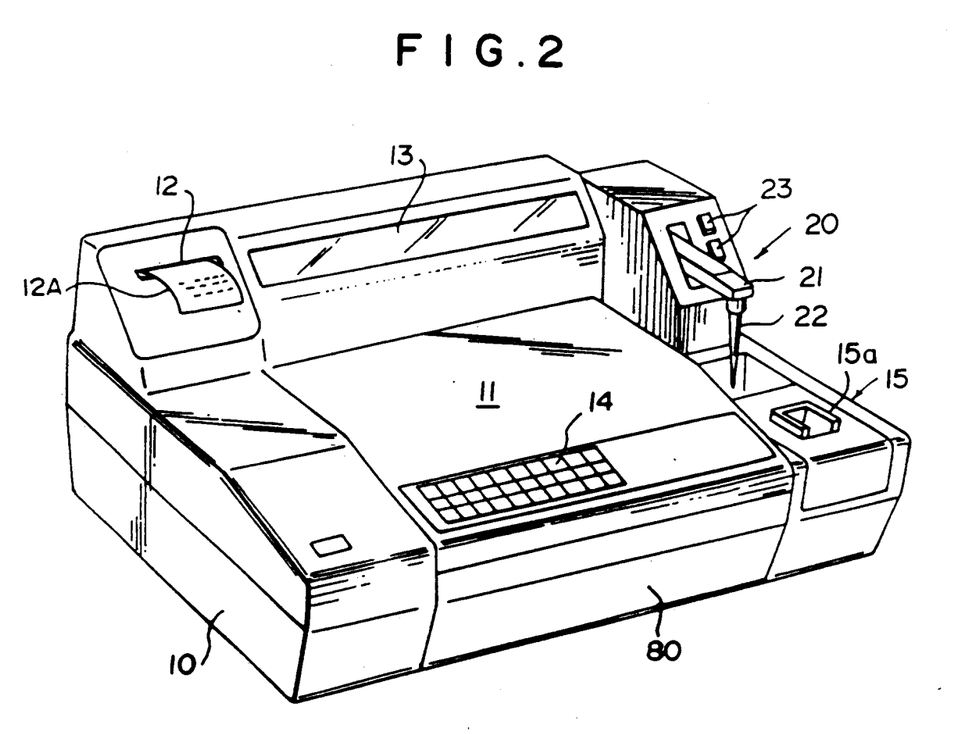
FIG. 2 is a perspective view showing an example of a biochemical analysis apparatus wherein the embodiment of the method for judging errors in applying a liquid sample during a biochemical analysis in accordance with the present invention is employed.

FIG. 2 is a perspective view showing an example of a biochemical analysis apparatus wherein an embodiment of the method for judging errors in applying a liquid sample during a biochemical analysis in accordance with the present invention is employed.

With reference to FIG. 2, an incubator, a slide conveyance means, a slide feed-in means, and the like, are disposed in a main body 10, and covered with a cover 11. A display section 13 for displaying the measured values, or the like, a feed-out opening 12 for a sheet 12A on which the displayed information is printed, and an operating key section 14 for controlling the displaying, or the like, are located on the outer side of the chemical analysis apparatus. A slide guide 15a for holding unused chemical analysis slides is located at a slide stand-by section 15 on the right side of the chemical analysis apparatus. A plurality of unused chemical analysis slides are held in the stacked form by the slide guide 15a. Alternatively, a cartridge housing a plurality of chemical analysis slides may be fitted to the slide guide 15a. A sample application means 20 for applying a predetermined liquid sample onto a reagent layer of a chemical analysis slide is located at the rear of the slide stand-by section 15. The sample application means 20 is composed of a sample application arm 21, which projects forwardly and which can rotate vertically around its rear edge, a sample application pipette 22 extending downward from the front end of the sample application arm 21, and operating pushbuttons 23, 23 for controlling the vertical movement of the sample application arm 21 and the drawing-in and discharging of the liquid sample in the sample application pipette 22. In the course of sample application by the sample application means 20, the sample application arm 21 is rotated up to move the sample application pipette 22 up by the operation of the operating buttons 23, 23. The lower edge of the sample application pipette 22 is then dipped in a liquid sample contained in a vessel, and a predetermined amount of the liquid sample is drawn into the sample application pipette 22. Then, the sample application arm 21 is rotated down, and the predetermined amount of the liquid sample is applied from the sample application pipette 22 onto the reagent layer of a chemical analysis slide, which is located below the sample application pipette 22.

Figure 3:
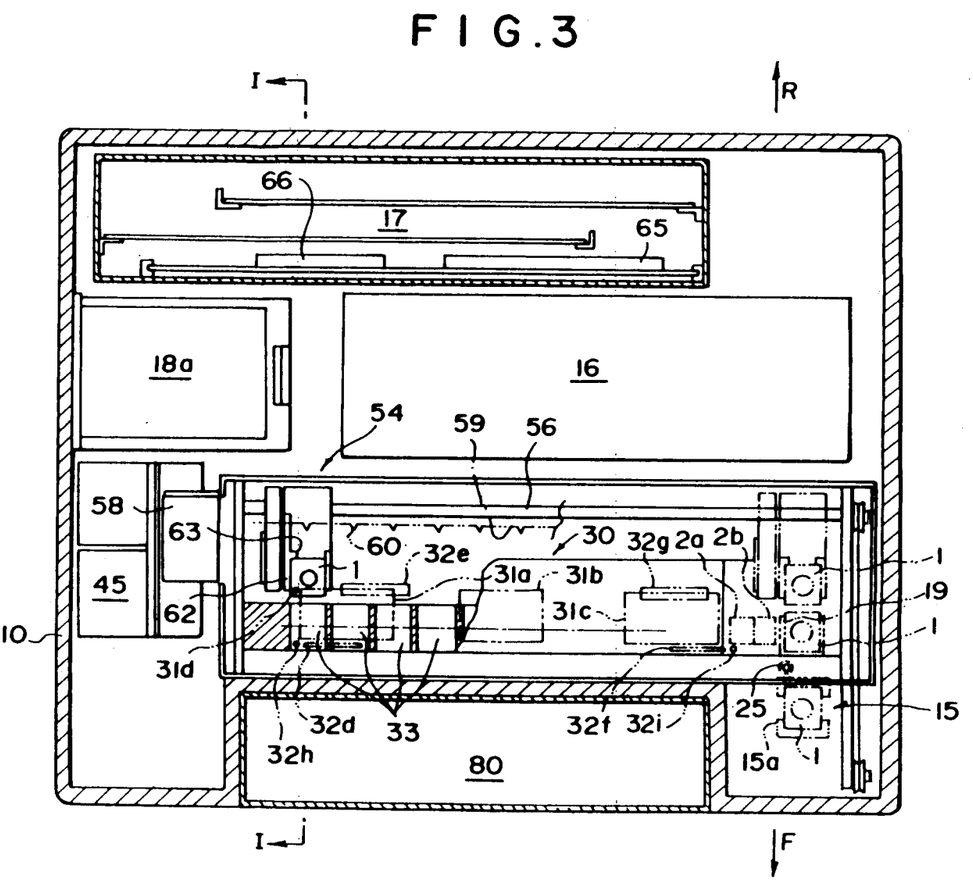
FIG. 3 is a plan view showing the major part of the biochemical analysis apparatus shown in FIG. 2, with a cover thereof being omitted.
Figure 4:
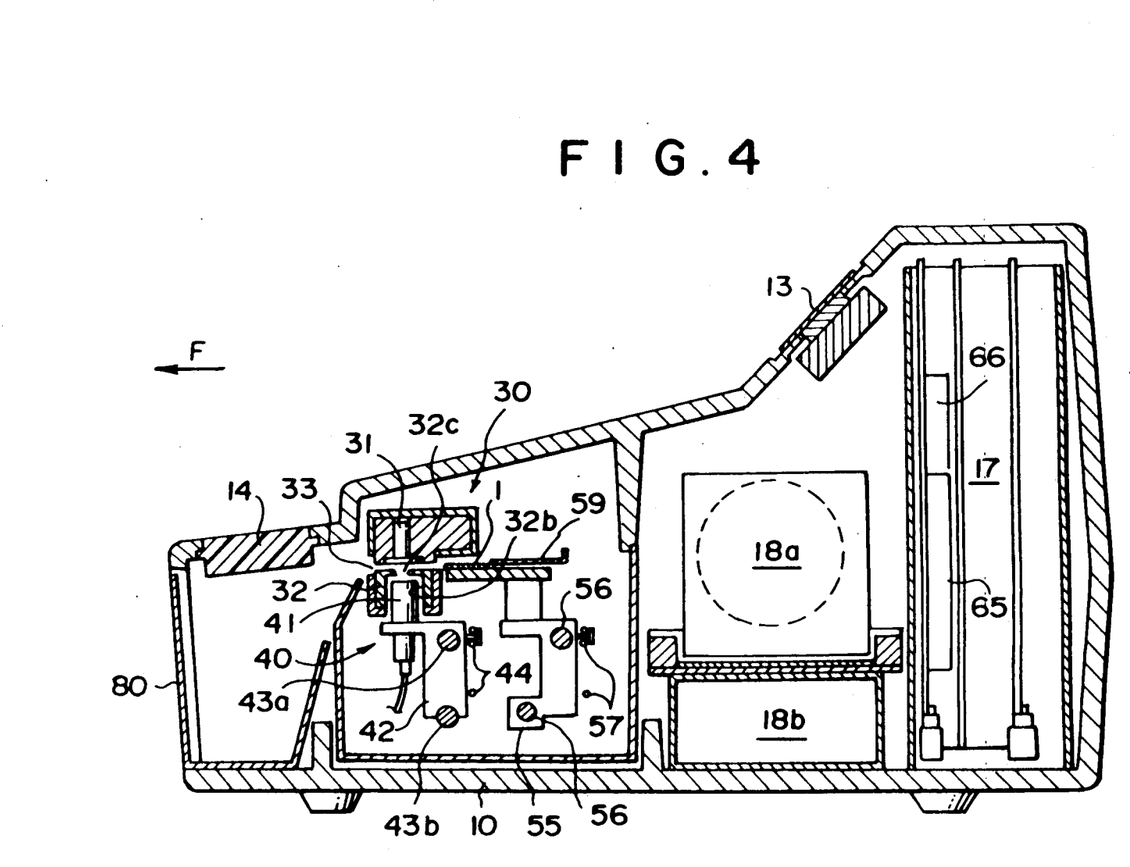
FIG. 4 is a sectional view taken along line I—I of FIG. 3.

FIG. 3 is a plan view showing the major part of the biochemical analysis apparatus shown in FIG. 2, with a cover thereof being omitted. FIG. 4 is a sectional view taken along line I—I of FIG. 3. The internal configuration of the chemical analysis apparatus will hereinbelow be described with reference to FIGS. 3 and 4.

An incubator 30 for incubating a chemical analysis slide 1, to which a liquid sample has been applied by the sample application means 20, is located inside of the biochemical analysis apparatus. Also, a measurement means 40 for finding the extent of a color reaction occurring in a chemical analysis slide 1, which has been incubated, i.e. the reflection density of the chemical analysis slide 1, which has been incubated, is located inside of the biochemical analysis apparatus. Further, a slide conveyance means, which conveys chemical analysis slides 1, 1, ... from the slide stand-by section 15 to compartments 33, 33, ... of the incubator 30 is located inside of the chemical analysis apparatus. The slide conveyance means will later be described in detail with reference to FIG. 6. The chemical analysis apparatus is also provided with an electric power source 16, a printed circuit board 17 for a control circuit, a light source 18a for the measurement means 40, and a magnetic disk drive mechanism 18b. In the description below, the direction indicated by the arrow F is referred to as the forward direction or the front side, and the direction indicated by the arrow R is referred to as the backward direction or the rear side. Also, the right side and the left side are referred to with respect to FIG. 3.

The incubator 30 extends in the transverse (i.e. rightward-leftward) direction, and a plurality of the compartments 33, 33, . . . are located side by side in the transverse direction in the incubator 30. The compartments 33, 33, . . . are provided with inlet openings and outlet openings. The inlet openings are located side by side in the transverse direction on the rear side of the compartments 33, 33, . . . . The outlet openings are located side by side in the transverse direction on the front side of the compartments 33, 33, . . . . A chemical analysis slide 1 is fed into a compartment 33 from its inlet opening, and ejected from its outlet opening. The chemical analysis slide 1, which has been ejected from the outlet opening, is discharged into an ejection box 80, which is located in front of the incubator 30. Also, the compartments 33 are provided with a lower member 32 for supporting the chemical analysis slides 1, 1, . . . thereon, and an upper member 31 for holding the chemical analysis slides 1, 1, . . . which are supported on the lower member 32, from above. The chemical analysis slides 1, 1, . . . are incubated by the upper member 31 and the lower member 32.

The lower member 32 defines a long groove 32b, which extends in the transverse direction and which accommodates a probe 41 for determining the reflection densities of chemical analysis slides 1, 1, . . . accommodated in the compartments 33, 33, . . . . The lower member 32 is also provided with openings 32c, 32c, . . . through which the probe 41 irradiate light to the chemical analysis slides 1, 1, . . . during the determination of the reflection densities.

Figure 7:
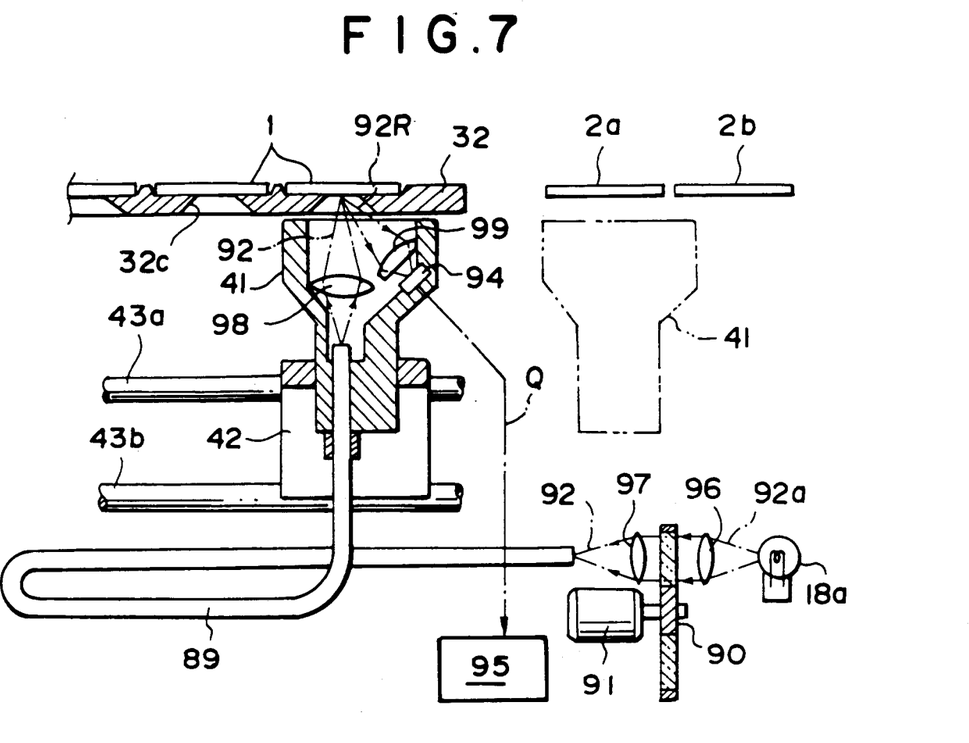
FIG. 7 is a schematic front view showing a probe and surrounding parts of the biochemical analysis apparatus shown in FIG. 2.
Figure 8:
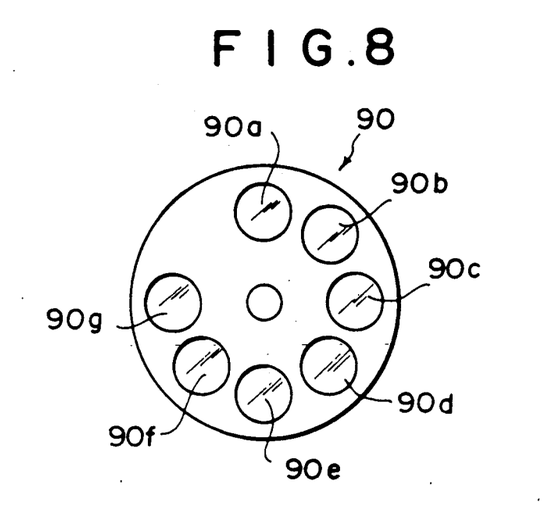
FIG. 8 is a plan view showing a filter plate of the probe.

The probe 41 is supported on a supporting base 42. A wire 44 is connected to the supporting base 42 and is pulled by a motor 45. In this manner, the supporting base 42 is moved in the long groove 32b in the transverse direction by being guided by guide rods 43a and 43b. The probe 41 moves together with the supporting base and determines the reflection density of each chemical analysis slide 1, which is accommodated in each compartment 33. The probe 41 will hereinbelow be described in detail with reference to FIG. 7. One edge of an optical fiber 89 is connected to the probe 41. The other edge of the optical fiber 89 is secured at the position facing the light source 18a. The light source 18a produces light 92a. The light 92a is collimated by a collimator lens 96, and the collimated light passes through a filter plate 90. Light 92, which has passed through the filter plate 90, is then condensed by a condensing lens 97 and impinges upon the other edge of the optical fiber 89. By way of example, as shown in FIG. 8, the filter plate 90 is provided with interference filters 90a, 90b, 90c, 90d, 90e, 90f, and 90g. The filter plate 90 is rotated by a pulse motor 91, and one of the interference filters 90a through 90g is selectively located in the optical path of the light 92a. Each of the interference filters 90a through 90g transmits light having inherent wavelengths in accordance with the combination of the reagent contained in a chemical analysis slide 1 with the liquid sample, which is to be analyzed.

The light 92, which has passed through one of the interference filters 90a through 90g and which now has predetermined wavelengths, is guided by the optical fiber 89 and radiated out of on edge of the optical fiber 89 in the probe 41. The light 92 is then condensed by a condensing lens 98 and irradiated to a chemical analysis slide 1. Light 92R reflected by the chemical analysis slide 1 is condensed by a condensing lens 99 and received by a photodetector 94. The photodetector 94 detects the amount of the reflected light 92R and generates an output Q. The output Q is fed into a measurement circuit 95, which carries out processing, such as amplification and digitization, on the output Q and generates information about the amount of the reflected light 92R.

The probe 41 also moves to the positions below a white reference plate 2a and a black reference plate 2b, which serve as reference density plates. Therefore, the measurement means 40 can also measure the amounts of light reflected by the white reference plate 2a and the black reference plate 2b. The amounts of the reflected light thus measured are used during the correction of values obtained from analyses. Also, when a chemical analysis slide 1 is conveyed by a slide pushing lever 52, which will be described later, from the slide stand-by section 15, the probe 41 moves to the position below a feed base 19, which will be described later. In this manner, the background density of the chemical analysis slide 1, i.e. the reflection density of the chemical analysis slide 1 to which no liquid sample has been applied, is determined. A bar code reader 25 is located below part of the slide conveyance path between the slide stand-by section 15 and the feed base 19. When a chemical analysis slide 1 passes over this part of the slide conveyance path, the bar code reader 25 reads the bar code representing the kind of the reagent contained in the chemical analysis slide 1, the lot number of the chemical analysis slide 1, or the like, which bar code is recorded on a mount of the chemical analysis slide 1.

Figure 5:
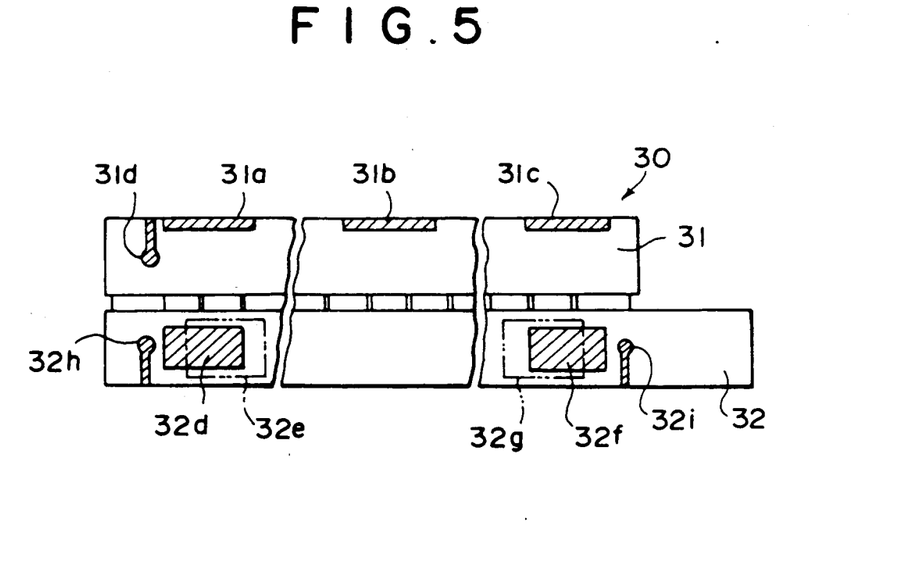
FIG. 5 is a front view showing an incubator.

FIG. 5 is a front view of the incubator 30 and shows how heaters for keeping the incubator 30 at a predetermined temperature are located. How the heaters are located will hereinbelow be described with reference to FIGS. 3, 4, and 5.

Heaters 32d, 32e, 32f, and 32g are located in the vertical orientation in the vicinity of both edges of the lower member 32 of the incubator 30, which edges are taken in the transverse direction. The heaters 32d, 32e, 32f, and 32g are located at the parts of the lower member 32, which extend downwardly with the groove 32b shown in FIG. 4 intervening therebetween. A temperature sensor 32h is located on the left side of the heater 32d. The left heaters 32d and 32e are controlled such that the temperature sensor 32h indicates a predetermined temperature. A temperature sensor 32i is located on the right side of the heater 32f. The right heaters 32f and 32g are controlled such that the temperature sensor 32i indicates the predetermined temperature.

Heaters 31a, 31b, and 31c are located in the horizontal orientation at the upper member 31 of the incubator 30. A temperature sensor 31d is located on the left side of the heater 31a. The heaters 31a, 31b, and 31c uniformly heat the incubator 30 from above and are controlled such that the temperature sensor 31d indicates the predetermined temperature.

Figure 6:
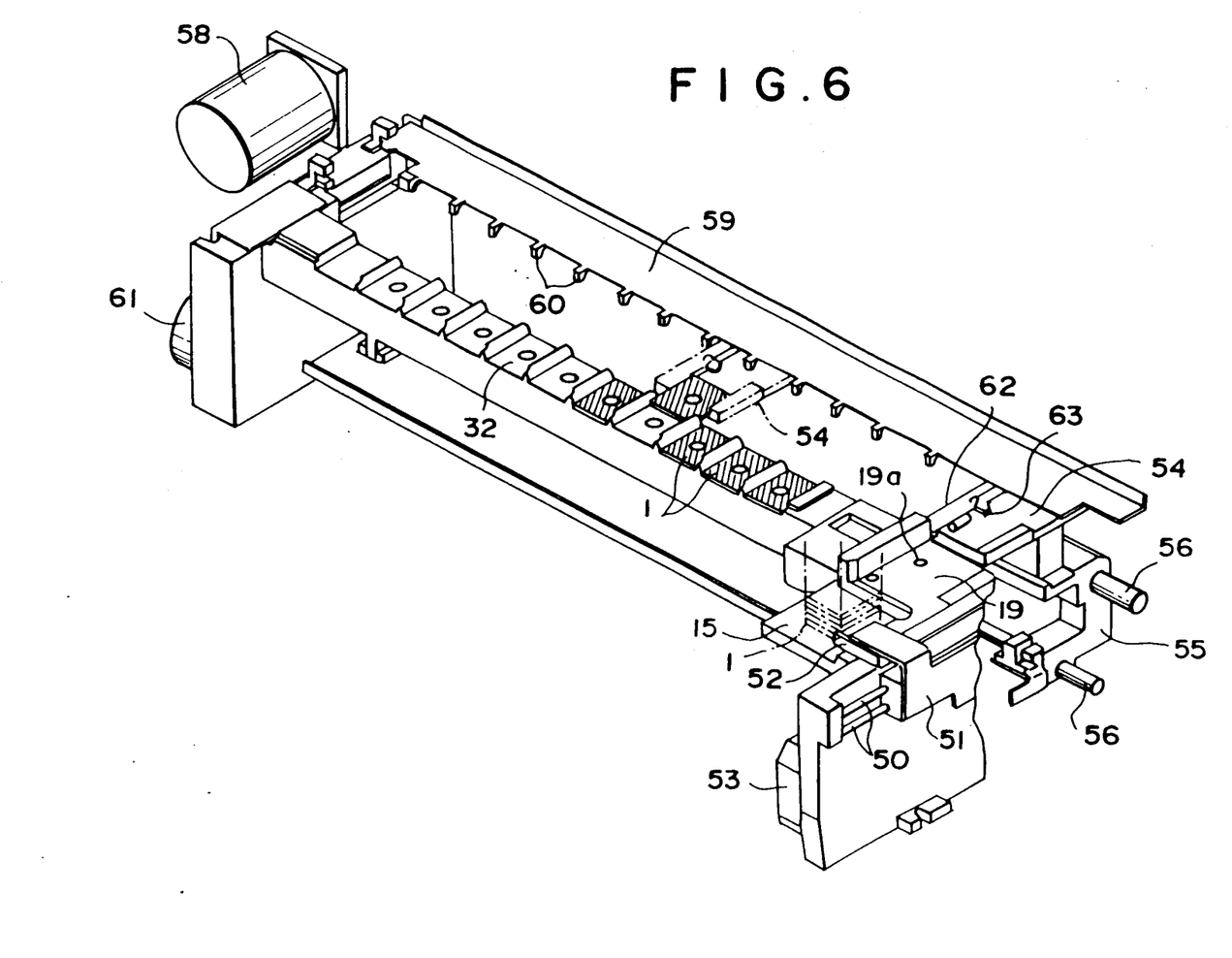
FIG. 6 is a perspective view showing a slide conveyance means of the biochemical analysis apparatus shown in FIG. 2.

The slide conveyance means will hereinbelow be described with reference to FIG. 6. Guide rods 50, 50 extend in the forward-backward direction. A block 51 is supported so that it can move along the guide rods 50, 50. The block 51 is provided with the slide pushing lever 52. The block 51 is moved forwardly and backwardly by a pushing lever operating motor 53. The feed base 19 is located at the rear of the slide stand-by section 15. A shuttle 54, which moves in the transverse direction, is located at the rear of the feed base 19. The shuttle 54 is secured to the upper part of a supporting base 55, which can move along guide rods 56, 56. Part of an endless wire 57 shown in FIG. 4 is secured to the supporting base 55. When the wire 57 is rotated by a shuttle operating motor 58, the supporting base 55 and the shuttle 54 are moved in the transverse direction. A slide feed-in bar 59 is supported above the shuttle 54 such that it can move forwardly and backwardly. Also, the slide feed-in bar 59 is provided with feed-in projections 60, 60, . . . at the positions facing the inlet openings of the compartments 33, 33, . . . of the incubator 30. The slide feed-in bar 59 is moved by a feed-in bar operating motor 61.

How the slide conveyance means operates will be described hereinbelow. First, the block 51 is located at the position shown in FIG. 6. At this time, the slide pushing lever 52 is located in front of the slide standby section 15. The pushing lever operating motor 53 is then activated, and the block 51 moves backwardly. The lowest chemical analysis slide 1 among the chemical analysis slides 1, 1, . . . , which are stacked in, for example, a cartridge at the slide stand-by section 15, is pushed by the slide pushing lever 52 onto the feed base 19. The feed base 19 has an opening 19a, through which the probe 41 irradiates light to the chemical analysis slide 1. In this manner, the background density of the chemical analysis slide 1 is determined.

Thereafter, the sample application pipette 22 applies a predetermined amount of a liquid sample to the chemical analysis slide 1. The slide pushing lever 52 further moves backwardly and transfers the chemical analysis slide 1 onto the shuttle 54. The direction along which the pushing lever operating motor 53 rotates is thereafter reversed, and the block 51 returns to the position shown in FIG. 6. Before the block 51 thus returns, the slide pushing lever 52 rotates such that its leading edge faces backwardly. Therefore, when the block 51 returns, the slide pushing lever 52 does not move a chemical analysis slide 1 located in the slide stand-by section 15.

After the chemical analysis slide 1 is placed on the shuttle 54 in the manner described above, the shuttle operating motor 58 is activated to move the shuttle 54 to the position facing a predetermined compartment 33, into which the chemical analysis slide 1 is to be fed. Thereafter, the feed-in bar operating motor 61 is activated to move the slide feed-in bar 59 forwardly by a predetermined distance from the position shown in FIG. 6. As a result, the chemical analysis slide 1 on the shuttle 54 is pushed forwardly by a feed-in projection 60 of the slide feed-in bar 59. The chemical analysis slide 1 passes through the inlet opening of the corresponding compartment 33 and is accommodated in the compartment 33. At this time, if a chemical analysis slide 1, which has been used in the analysis, is present in the compartment 33, it will be pushed by the new chemical analysis slide 1 into the ejection box 80.

The chemical analysis slide 1, which has been accommodated in the compartment 33 in the manner described above, is incubated. The optical density of the chemical analysis slide 1, which depends on how much of a reaction product was formed by the reaction between the liquid sample and the reagent in the chemical analysis slide 1, is found with the probe 41.

In this example, one of the members, which guide the right and left edges of the chemical analysis slide 1 on the shuttle 54, serves as a slide ejection lever. Therefore, a chemical analysis slide 1, which has been accommodated in each compartment 33 during the last analysis among a series of analysis operations, can be discharged from the compartment 33 by the slide ejection lever. Specifically, a slide ejection lever 62 having a projection 63 on its inner surface is located on the shuttle 54 so that it can move forwardly and backwardly. The slide ejection lever 62 is urged backwardly by an urging means (not shown). When the last chemical analysis slide 1 is to be discharged from the compartment 33, the shuttle 54 is moved to a position at which the slide ejection lever 62 faces the middle part of the compartment 33. When the slide feed-in bar 59 moves forwardly in the manner described above, its feed-in projection 60 comes into contact with the projection 63 and pushes the slide ejection lever 62 forwardly. As a result, the slide ejection lever 62 moves forwardly against the urging force of the urging means and discharges the chemical analysis slide 1 from the compartment 33 into the ejection box 80.

Figure 1:
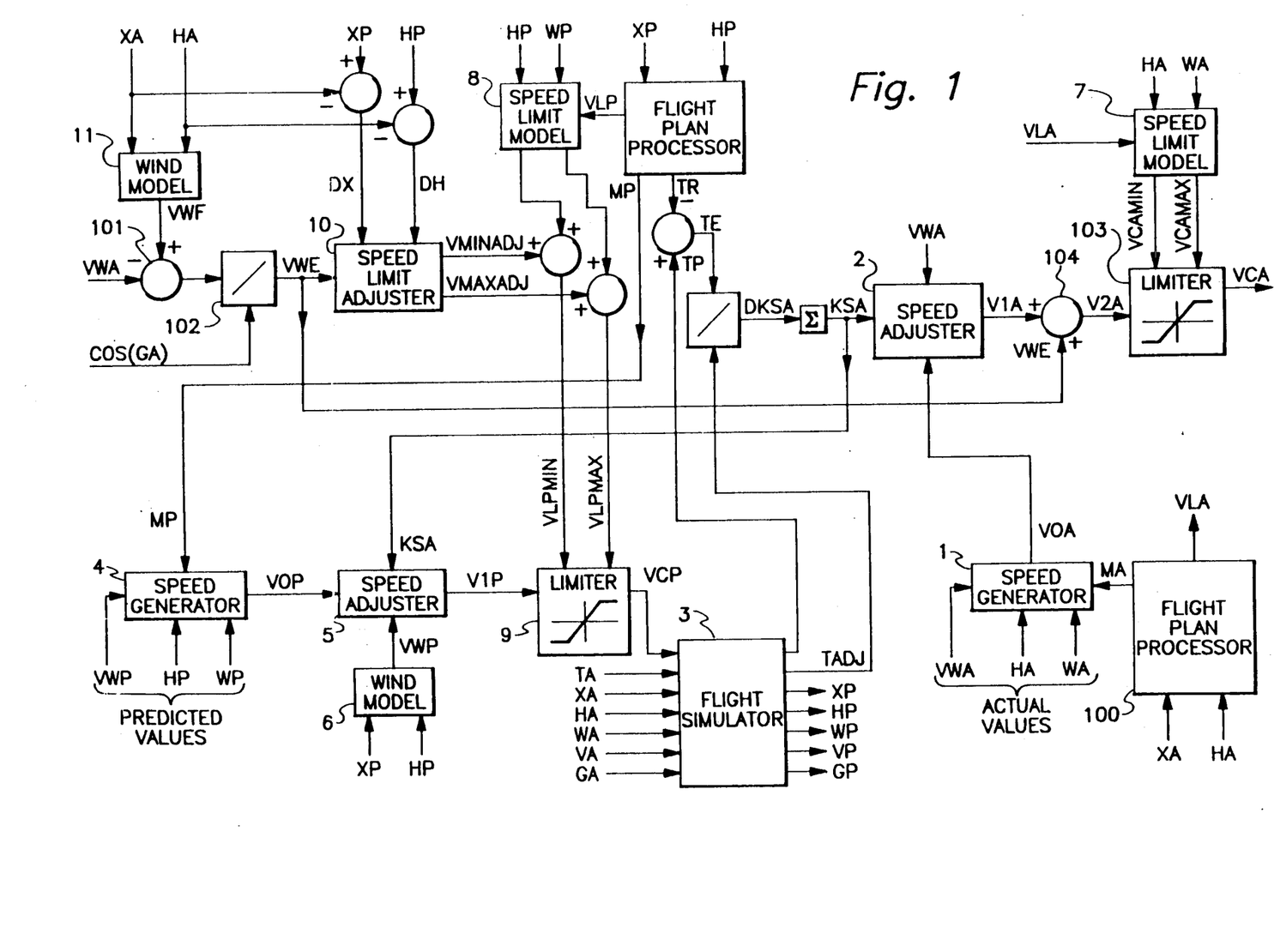
FIG. 1 is a flow chart showing a process for determining the concentration of a specific constituent, wherein an embodiment of the method for judging errors in applying a liquid sample during a biochemical analysis in accordance with the present invention is employed.

FIG. 1 shows the process for determining the concentration D of a specific constituent, which process is controlled by a control means 66 shown in FIGS. 3 and 4. In FIG. 1, as an aid in facilitating the explanation, how the conveyance of the chemical analysis slides 1, 1, . . . is controlled is omitted.

With reference to FIG. 1, the process is begun in a step P1. In a step P2, the number i representing the sequence of measurement of the amount of reflected light is set to "1". In a step P3, the sample application pipette applies a liquid sample to a chemical analysis slide 1. Thereafter, in a step P4, light is irradiated by the probe 41 to the chemical analysis slide 1, and the amount of light reflected thereby is measured. The measurement of the amount of reflected light is also carried out for the white reference plate 2a and the black reference plate 2b. The measurement circuit 95 generates information about measured values S, W, and B representing the amounts of light reflected by the chemical analysis slide 1, the white reference plate 2a, and the black reference plate 2b. The information about the measured values S, W, and B is fed into an operation means 65. Thereafter, in a step P5, the operation means 65 calculates the reflection density OD of the chemical analysis slide 1 from the measured values S, W, and B. The calculation is carried out with the formula $$OD = \log\left(\frac{W - B}{10^{-OD_w}(S - B) - 10^{-OD_b}(S - W)}\right)$$

where W denotes the measured value representing the amount of light reflected by the white reference plate 2a, B denotes the measured value representing the amount of light reflected by the black reference plate 2b, S denotes the measured value representing the amount of light reflected by the chemical analysis slide 1, ODw denotes the reflection density of the white reference plate 2a determined with a reference density meter, and ODb denotes the reflection density of the black reference plate 2b determined with a reference density meter.

In a step P6, information about the reflection density OD1 obtained from the calculation is stored in an internal memory of the operation means 65.

Thereafter, in a step P7, a judgment is made as to whether a predetermined analysis time (e.g. 5 to 6 minutes), which is inherent to the specific constituent to be analyzed, has or has not occurred. During several initial measurements, because the predetermined analysis time has not occurred in the step P7, the procedure returns to the step P4. At this time, in a step P8, the number i changes from "1" to "2". In the manner described above, for a single chemical analysis slide 1, the measurement of the amount of the reflected light is carried out at intervals of, for example, 10 to 15 seconds, and is finished within a predetermined time (e.g. 5 to 6 minutes). When n number of measurements of the reflection densities OD have been carried out and the predetermined analysis time T has occurred in the step P7, the measurements of the reflection densities OD of the chemical analysis slide 1 are completed, and the process proceeds to a step P9.

In the step P9, the operation means 65 reads the information about reflection densities OD1, OD2, OD3, . . . , ODn from the memory. Thereafter, in a step P10, the operation means 65 calculates the difference S between the maximum value ODmax and the minimum value ODmin of the reflection densities OD1, OD2, OD3, . . . , ODn. In a step P11, the operation means 65 compares the difference S with a predetermined threshold value Th. In cases where $S \geq Th$, it is judged that the liquid sample was normally applied to the chemical analysis slide 1, and the process proceeds to a step P12, in which the concentration D of the specific constituent is calculated. In cases where $S < Th$, it is judged that errors occurred in applying the liquid sample to the chemical analysis slide 1, and the process proceeds to a step P14, in which information about the errors is displayed and recorded.

Figure 9:
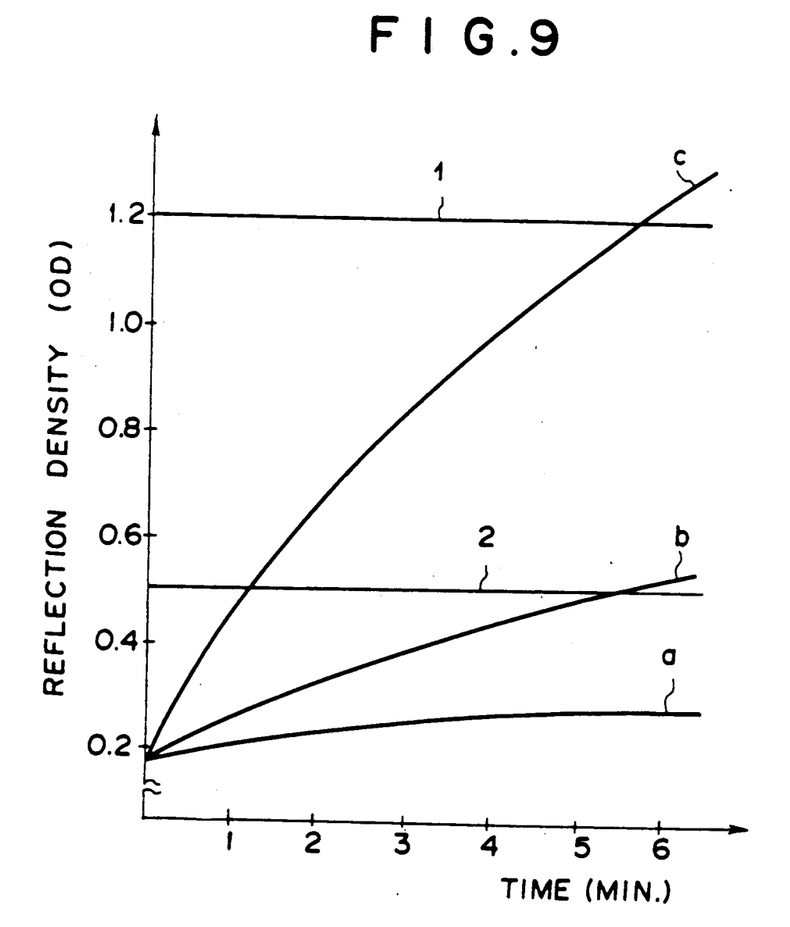
FIG. 9 is a graph showing how the optical densities of analysis media change with the passage of time.

The reason why errors in applying a liquid sample to a chemical analysis slide can be judged will be described hereinbelow with reference to FIG. 9. FIG. 9 shows how the optical densities OD of analysis media change with the passage of time while the analysis media are being incubated during the determination of the concentrations of glucose in blood. In this example, the guaranteed range of glucose concentrations, which can be determined accurately with the biochemical analysis apparatus, is 10 mg/dl to 600 mg/dl. As indicated by curves b and c in FIG. 9, in cases blood containing glucose in concentrations falling within the guaranteed range was applied to analysis media, the reflection densities OD of the analysis media increase monotonously with the passage of time while the analysis media are being incubated. Also, as indicated by curve a in FIG. 9, in cases blood containing glucose in a concentration (1 mg/dl) beyond the guaranteed range was applied to an analysis medium, the reflection density OD of the analysis medium increases monotonously, and the difference S between the maximum value ODmax and the minimum value ODmin of the reflection densities reaches approximately 0.1.

In FIG. 9, curves 1 and 2 indicate the changes in the reflection densities OD, which are determined when no liquid sample was applied to analysis media. When no liquid sample was applied to analysis media, the reflection densities OD do not change monotonously and are approximately constant. In such cases, a change in the reflection densities OD is the one caused by fluctuations in the conditions under which the measurement is carried out. Therefore, the difference S between the maximum value ODmax and the minimum value ODmin of the reflection densities is 0.0003 for curve 1, and is 0.0007 for curve 2.

Accordingly, during the determination of the concentration of glucose, in the step P11 shown in FIG. 1, the threshold value Th may be set as being, for example, 0.001. In such cases, when $S < Th$, it can be judged that errors occurred in applying the liquid sample to the chemical analysis slide 1. When $S \geq Th$, it can be judged that the liquid sample was normally applied to the chemical analysis slide 1.

In cases where it is judged that the liquid sample was normally applied to the chemical analysis slide 1, the operation means 65 finds the optical density of the chemical analysis slide 1 at the time when, for example, the predetermined analysis time has occurred. The optical density is determined from the reflection densities OD1 through ODn, which have been found in the manner described above. From the optical density thus found, the concentration D of the specific constituent is determined with a predetermined calibration curve.

The operation means 65 feeds a signal, which represents the concentration D thus determined, to the control means 66. In a step P13, the control means 66 works to display the information about the concentration represented by the signal on the display section 13, and to print the information about the concentration on the recording sheet 12A by a printer (not shown). The recording sheet 12A is discharged from the ejection opening 12 shown in FIG. 2.

In cases where the operation means 65 judges that errors occurred in applying the liquid sample to the chemical analysis slide 1, the control means 66 works to display the information about the errors on the display section 13 or to print the information about the errors on the recording sheet 12A. By way of example, an "error" message or a "found value=xxxxx" message is displayed or recorded. After the information about the correct concentration thus found or the information about the errors in applying the liquid sample to the chemical analysis slide 1 is displayed or recorded, the process for determining the concentration of the specific constituent is completed in a step P15.

In the embodiment described above, a judgment is made as to whether the liquid sample was or was not applied to the chemical analysis slide 1. Alternatively, the threshold value Th may be selected appropriately such that a judgment can be made as to whether a predetermined amount or an insufficient amount of a liquid sample was applied to a chemical analysis slide 1. Specifically, as indicated by curve b in FIG. 9, in cases where a predetermined amount of a liquid sample containing glucose in a concentration of 10 mg/dl (which corresponds to the minimum of the guaranteed range of glucose concentrations) was applied normally to a chemical analysis slide 1, the difference S between the maximum value ODmax and the minimum value ODmin of the reflection densities reaches approximately 0.35 when the analysis time of 6 minutes has occurred. If a difference S markedly smaller than 0.35 is obtained during a biochemical analysis, it may be thought that the predetermined amount of a liquid sample containing glucose in a low concentration (e.g. 1 mg/dl) was applied correctly to a chemical analysis slide 1, or that an insufficient amount of a liquid sample was applied to the chemical analysis slide 1. Therefore, in order for the reliability of biochemical analyses to be kept high, it is desirable that concentrations found from biochemical analyses, which go beyond the guaranteed range of 10 mg/dl to 600 mg/dl (i.e. lower than 10 mg/dl) and which may be incorrect, are not outputted as found values. For this purpose, the threshold value Th may be set as being, for example, 0.2. When S<Th, it may be judged that errors occurred in applying the liquid sample to the chemical analysis slide 1. In FIG. 9, curve c indicates the change in the reflection density OD of an analysis medium, which change occurs with the passage of time while the analysis medium is being incubated after a predetermined amount of a liquid sample containing glucose in a concentration of 600 mg/dl (which corresponds to the maximum of the guaranteed range of glucose concentrations) was applied normally to the analysis medium.

The method for judging errors in applying liquid samples during biochemical analyses in accordance with the present invention is applicable also when test films are utilized in biochemical analysis operations.

I claim:

1. A method for judging errors in applying a liquid sample during a biochemical analysis wherein a droplet of liquid sample is applied to an analysis medium containing a reagent, which chemically reacts with a specific constituent in the liquid sample, the analysis medium is then incubated, the optical densities of the analysis medium are determined, and concentration of the specific constituent in the liquid sample is determined from the optical densities of the analysis medium thus determined, the method for judging errors in applying a liquid sample during a biochemical analysis comprising the steps of:

i) determining the optical density of said analysis medium plural times with the passage of time while said analysis medium is being incubated,
   ii) calculating the difference between the maximum value and the minimum value of the optical densities thus determined for said analysis medium,
   iii) comparing said difference with a predetermined threshold value, and
   iv) in cases said difference is smaller than said threshold value, judging that errors occurred in applying a liquid sample to said analysis medium.

2. A method as defined in claim 1 wherein said analysis medium is a chemical analysis slide.

3. A method as defined in claim 1 wherein said analysis medium is a long test film.

4. A method as defined in claim 1 wherein said optical densities of said analysis medium are determined by use of the formula $$OD = \log\left(\frac{W-B}{10^{-OD_w}(S-B) - 10^{-OD_b}(S-W)}\right)$$

where W denotes the measured value representing the amount of light reflected by a white reference plate, B denotes the measured value representing the amount of light reflected by a black reference plate, S denotes the measured value representing the amount of light reflected by the analysis medium, ODw denotes the reflection density of the white reference plate determined with a reference density meter, and ODb denotes the reflection density of the black reference plate determined with a reference density meter.

* * * * *